United States Patent [19]
Abel

[11] Patent Number: 6,093,192
[45] Date of Patent: Jul. 25, 2000

[54] TARGET DEVICE FOR PROXIMAL AND DISTAL LOCKING OF MEDULLARY NAILS WITHOUT X-RAYS

[75] Inventor: Christian Abel, Berlin, Germany

[73] Assignee: aap Implanate Aktiengesellschaft, Berlin, Germany

[21] Appl. No.: 09/298,214

[22] Filed: Apr. 23, 1999

[30] Foreign Application Priority Data

Apr. 24, 1998 [DE] Germany ................. 198 19 168

[51] Int. Cl.[7] .............................................. A61B 17/56
[52] U.S. Cl. ................................................. 606/98
[58] Field of Search .................... 606/53, 80, 86, 606/87, 96, 97, 98, 102, 104, 62, 64

[56] References Cited

U.S. PATENT DOCUMENTS

| | | | |
|---|---|---|---|
| 4,667,664 | 5/1987 | Taylor et al. | 606/64 |
| 4,865,025 | 9/1989 | Buzzi et al. | 606/96 |
| 5,474,561 | 12/1995 | Yao | 606/98 |

FOREIGN PATENT DOCUMENTS

4240277A1  9/1993  Germany .

*Primary Examiner*—Michael Buiz
*Assistant Examiner*—David O. Reip
*Attorney, Agent, or Firm*—Cohen, Pontani, Lieberman & Pavane

[57] ABSTRACT

The invention is directed to a target device for proximal and distal locking of medullary nails without X rays. The proximal and the distal target devices each have a U-shaped part, wherein guide bores are disposed in the widened end areas of the legs of the U-shaped parts. The medullary nail is fixedly connected with the proximal target device via a crosspiece and the proximal target device is connected with the distal target device by a pivotable and adjustable spacer. The distance of the end of the medullary nail from the distal target device is adjusted by a spacer element such that the center axes of the guide bores in the target devices are aligned with the center axes of channels or bores in the medullary nail, which channels communicate with the guide bores. The spacer is adjustable in a telescoping manner, and a rigid connection element connects a leg of the U-shaped proximal target device with a leg of the U-shaped distal target device in the plane of the center axes of the guide bores or medullary nail channels. The connection element is mounted so as to be rotatable at the leg of the U-shaped proximal and distal target device, and the spacer is arranged so as to be pivotable at the proximal target device via a joint vertical to the plane of the center axes of the guide bores and medullary nail channels.

5 Claims, 2 Drawing Sheets

TARGET DEVICE FOR PROXIMAL AND DISTAL LOCKING OF MEDULLARY NAILS WITHOUT X-RAYS

BACKGROUND OF THE INVENTION

1. Field of the Invention

The present invention relates to the fixation of medullary nails within bones, and more particularly, to a target device for the proximal and distal locking of medullary nails without X-rays.

2. Description of the Related Art

In order to prevent additional radiation loading of the operator, target devices for setting of locking screws in the medullary nail inserted in the bone are known. These target devices are rigidly connected with the medullary nail. The target device generally has guide bores through which the bone bore hole and the locking screw can be introduced so as to be exactly aligned with the contours of the bore hole and with the channels in the medullary nail.

Initially, however, only the proximal target device was fixedly connected with the medullary nail and a separate target device for placement of the distal locking screws had to be aligned by observing the same under X-ray. The current state of the art indicates that there are target devices which provide an additional fixed connection between the proximal and distal target devices.

Thus, according to DE 42 40 277 A1, an auxiliary rail is provided with guide holes for a bone drill to be applied and is screwed to the proximal end of the medullary nail. The guide holes are introduced in the auxiliary rail with a defined spacing analogous to the medullary nail. The auxiliary rail is fixed in its position relative to the bone in the area of the distal guide holes by means of fastening pins, e.g., Kirschner wire, and also with an intermediary of an additional bridge stirrup or clip.

DE 296 08 071 U1 goes a step further with respect to the fixing of the distal target device in that a spacer is provided in addition to a longitudinal target rail with which the distal target device is held at a predetermined distance from the proximal target device. The bore holes are aligned relative to the bore holes in the medullary nail by means of the spacer in a drill template fastened to the target rail. The Applicant's company manufactures a similar target arrangement in which the proximal and distal target device comprises, in each instance, a U-shaped part, wherein guide bores are introduced in the widened end areas of the legs of the U-shaped parts, the medullary nail is fixedly connected with the proximal target device via a crosspiece and an adjustable spacer is provided between the proximal and distal target device. The matching position of the guide bores of the distal target device with respect to the medullary nail channels which receive the locking screws is ensured by an adjustable and lockable spacer element which is guided through a bore in the bone so that it must rest against the medullary nail in the final position.

The alignment of the distal bore holes in the auxiliary rail and in the medullary nail is to be achieved according to DE 42 40 277 A1 by setting a thinner fastening pin through one of the bore holes beforehand followed by fixation by means of additional fastening pins anchored in the bone. The arrangement of a spacer element which is fastened to the distal target device and brought into contact with the medullary nail already offers substantially greater security for maintaining the alignment of the communicating bore holes. However, the following problem occurs in the latter solution: When the medullary nail bends during insertion into the un-drilled bone in the anterior or posterior direction, the distal target device 4 is lifted along with it via the spacer element 1 (FIG. 1) and pivots about the joint 3 at the proximal target device 5 via the spacer 2.

Referring to FIG. 1, assuming that the center of rotation of the nail 6 is located essentially in the area of the Herzog curvature 7, then the nail 6 and the spacer 2 have centers of rotation situated in different planes, wherein the planes are at a distance from one another corresponding to the length of the spacer 1.

It can be seen from FIG. 2 that when the target device and nail are deflected by the angle $\alpha$, the center axes of the bores in the distal target device move away from the correspondingly aligned center axes of the channels in the medullary nail by a distance x2 lying further toward the end of the nail. As a result, the channels are no longer aligned with inserted locking screws when a nail is bent (pivoted).

SUMMARY OF THE INVENTION

It is therefore an object of the invention to arrange the target device such that even in the case of a curved (pivoted) nail the distal target device takes part in the pivoting such that the alignment of the communicating bores in the target device and notches in the medullary nail is maintained.

This and other objects are achieved in accordance with an embodiment of the present invention wherein a proximal and distal target device each comprise a U-shaped part having guide bores disposed in widened end areas of legs of the U-shaped parts. The medullary nail is fixedly connected with the proximal target device via a crosspiece and the proximal target device is connected with the distal target device by a pivotable and adjustable spacer. The distance from the end of the medullary nail to the to the distal target device is adjusted by a spacer element such that a center axes of the guide bores in the respective target devices are aligned with center axes of medullary nail channels which communicate with the guide bores, and wherein the adjustable spacer is formed in two parts being slidably adjustable with respect to one another in a telescoping configuration. A connection element connects a leg of the U-shaped proximal target device with a leg of the U-shaped distal target device in a plane of the center axes of one of the guide bores and medullary nail channels, the connection element being rotatably mounted with respect to one of proximal and distal target devices, and a joint connects said adjustable spacer to the proximal target device such that the adjustable spacer is pivotable about said joint vertical to the plane of the center axes of the guide bores and medullary channels.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings wherein like reference numeral denote similar elements throughout the view.

DETAILED DESCRIPTION OF THE PRESENTLY PREFERRED EMBODIMENTS

Figure 1:
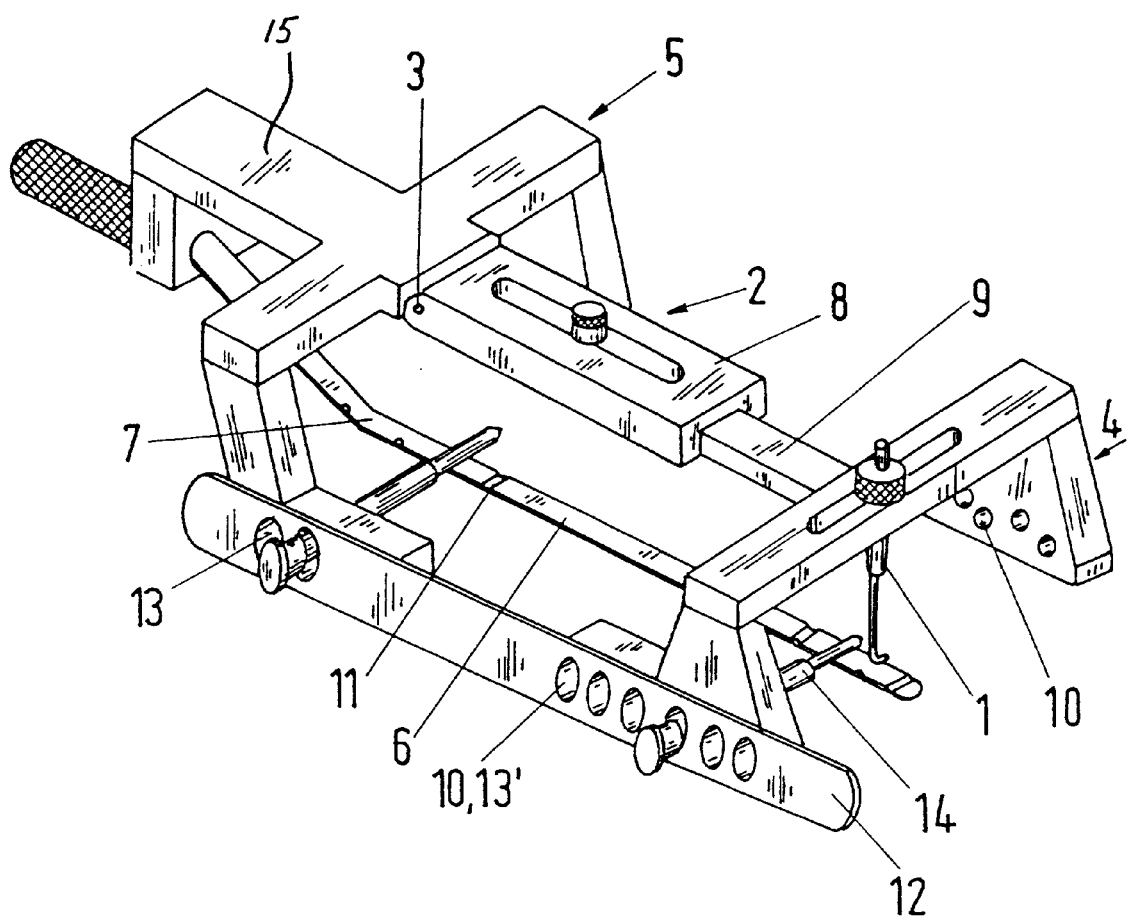
FIG. 1 is a perspective view of the target device according to an embodiment of the present invention.
Figure 2:
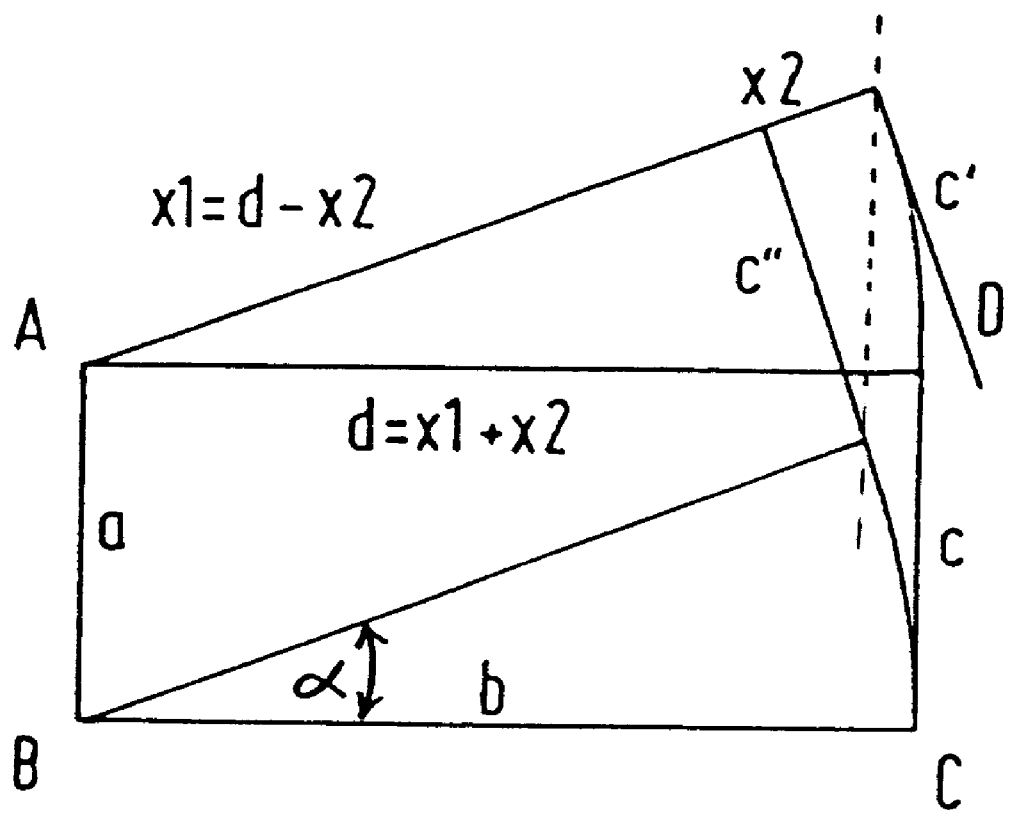
FIG. 2 is a schematic diagram of the length and position ratios of a medullary nail that is not curved and a curved (pivoted) medullary nail with respect to guide bores in the target device according to the present invention.

Referring to FIG. 1, a rigid connection element 12 connects the proximal target device 5 with the distal target device 4 such that the center of rotation for the distal target device 4 is situated in the plane of the center axes of the guide bores 10 or medullary nail channels 11. The medullary nail 6 is fixedly connected to the proximal target device via a crosspiece 15. Without this essential step of the present invention, the following problem can result: when the medullary nail 6 pivots in the region of the Herzog curvature 7 as a result of being inserted into the bone, the distal target device 4 is lifted via the spacer element 1. Referring to FIG. 2, the following is a list of terms depicted in FIG. 2.

A=center of rotation of the target device
B=center of rotation of the medullary nail
d=length of the spacer 2 without rotation
b=nail section
x2=length to be compensated
x1=length of spacer 2 after rotation and compensation according to the invention
c=spacer element 1 position without rotation in joints A and B
c'=spacer element 1 position after rotation in joints A and B
c"=spacer element 1 position after rotation in joints A and B and correct length compensation (according to the invention)

As can be seen from FIG. 2, the vertical projection of the end of the spacer 2 (depicted as c, c' and c") and therefore the projection of the guide bores 10 in the distal target device 4 are displaced further toward the end of the medullary nail 6. This results in the mis-alignment of the center axes of the guide bore holes 10 in the distal target device 4 and the center axes of the corresponding channels 11 in the medullary nail.

In the solution according to the present invention (FIG. 1), due to the connection element 12 which is rotatably mounted at the legs of the U-shaped part of the proximal 5 and distal 4 target device, the distal target device 4 pivots in the same plane as the medullary nail 6, i.e., the alignment of the center axes is maintained. During this pivoting, the spacer 2 becomes shorter in that part 9 of the spacer moves into part 8 in a telescoping manner. The shortening of spacer 2 compensates for the mis-alignment distance x2 shown in FIG. 2.

The connection element 12 according to the invention is constructed as a flat steel strip which has bore holes 13 at the proximal end and bores 13' at the distal end.

The connection element 12 is rotatably mounted at the leg of the U-shaped part of the proximal or distal target device (4, 5). The rotatable mounting of proximal or distal target devices 5 and 4, respectively can be implemented, for example, using a tissue protection sleeve 14 surrounding the locking screws which is inserted into the guide bores 10 during operation and which is additionally inserted through the bores 13, 13'.

In order to take into account the ventral or dorsal position of the medullary nail channels 11, the guide bores 10 in the leg of the U-shaped part of the target devices 4, 5 are arranged in two planes.

The respective distance between the proximal and distal target device 4, 5 can be adjusted, for example, in steps of 10 mm in that two bores 13 are disposed at the proximal end of the connection element 12 so as to be spaced apart by 10 mm and a plurality of bores 13' are disposed at the distal end of the connection element 12 at a distance of 20 mm from one another.

The invention is not limited by the embodiments described above which are presented as examples only but can be modified in various ways within the scope of protection defined by the appended patent claims.

I claim:

1. A target device for proximal and distal locking of a medullary nail without X-rays comprising:

a proximal and distal target device each comprising a U-shaped part having legs and guide bores disposed in widened end areas of said legs, the medullary nail being fixedly connected with the proximal target device via a crosspiece;

a pivotable and adjustable spacer connecting the proximal target device with the distal target device, said adjustable spacer being formed in two parts slidably adjustable with respect to one another in a telescoping configuration;

a spacer element adjusting a distance from an end of the medullary nail to the to the distal target device such that a center axes of the guide bores in the respective target devices are aligned with center axes of medullary nail channels which communicate with the guide bores;

a connection element connecting a leg of the U-shaped proximal target device with a leg of the U-shaped distal target device in a plane of the center axes of one of the guide bores and medullary nail channels, said connection element being rotatably mounted with respect to one of said proximal and distal target devices; and a joint connecting said adjustable spacer to the proximal target device such that said adjustable spacer is pivotable about said joint vertical to the plane of the center axes of the guide bores and medullary nail channels.

2. The target device in accordance with claim 1, wherein said connection element comprises a flat steel strip having bore holes disposed in respective ends thereof, said bore holes being spaced corresponding to a spacing of the guide bores.

3. The target device in accordance with claim 2, wherein said connection element further comprises two bore holes at one end being spaced 10 mm from each other, and a plurality of bore holes at the other end being spaced 20 mm from each other.

4. The target device in accordance with claim 1, wherein the guide bores in the legs of the U-shaped proximal and distal target devices are disposed in two planes to compensate for ventral and dorsal positions of the medullary nail channels.

5. The target device in accordance with claim 1, further comprising a tissue protection sleeve being inserted through said bore holes and said corresponding guide bores.

* * * * *